United States Patent
Hilal

(10) Patent No.: US 6,740,081 B2
(45) Date of Patent: May 25, 2004

(54) ELECTROSURGERY WITH IMPROVED CONTROL APPARATUS AND METHOD

(75) Inventor: Said Hilal, Coto de Caza, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 10/057,227

(22) Filed: Jan. 25, 2002

(65) Prior Publication Data

US 2003/0144654 A1 Jul. 31, 2003

(51) Int. Cl.⁷ ............................................. A61B 18/04
(52) U.S. Cl. ............................................. 606/34; 606/1
(58) Field of Search .............................. 606/1–2, 7–17, 606/27–52

(56) References Cited

U.S. PATENT DOCUMENTS

| | | | | |
|---|---|---|---|---|
| 3,775,638 A | | 11/1973 | Tidman | 315/36 |
| 4,040,426 A | | 8/1977 | Morrison, Jr. | 128/303.17 |
| 4,057,064 A | | 11/1977 | Morrison, Jr. et al. | 128/303.17 |
| 4,060,088 A | | 11/1977 | Morrison, Jr. et al. | 128/303.17 |
| 4,781,175 A | * | 11/1988 | McGreevy et al. | 606/40 |
| 4,901,720 A | * | 2/1990 | Bertrand | 606/40 |
| 5,507,724 A | * | 4/1996 | Hofmann et al. | 604/501 |
| 5,509,916 A | | 4/1996 | Taylor | 606/13 |
| 5,588,432 A | * | 12/1996 | Crowley | 600/439 |
| 5,599,296 A | * | 2/1997 | Spears | 604/26 |
| 5,704,908 A | * | 1/1998 | Hofmann et al. | 604/21 |
| 5,720,745 A | | 2/1998 | Farin et al. | 606/49 |
| 5,797,874 A | * | 8/1998 | Spears | 604/509 |
| 6,027,501 A | | 2/2000 | Goble et al. | 606/41 |
| 6,039,734 A | * | 3/2000 | Goble | 606/41 |
| 6,174,308 B1 | | 1/2001 | Goble et al. | 606/41 |
| 6,179,835 B1 | * | 1/2001 | Panescu et al. | 606/41 |
| 6,191,386 B1 | | 2/2001 | Albright et al. | 219/130.4 |
| 6,234,178 B1 | | 5/2001 | Goble et al. | 128/898 |
| 6,238,339 B1 | * | 5/2001 | Fiddian-Greene et al. | 600/309 |
| 6,387,088 B1 | * | 5/2002 | Shattuck et al. | 606/2 |
| 6,425,877 B1 | * | 7/2002 | Edwards | 604/21 |

* cited by examiner

Primary Examiner—Roy D. Gibson
Assistant Examiner—Peter J Vrettakos
(74) Attorney, Agent, or Firm—Richard L. Myers

(57) ABSTRACT

In electrosurgical system includes an electrosurgical generator providing power through an electrode, and a laser providing laser energy through an optical fiber. The electrode optical fiber and a source of environmental gas can all be included in a handpiece, catheter or other delivery device. In operation, the environmental gas can be released into the vicinity of an operative site and the laser activated to energize atoms along a pathway. Electrosurgical power can then be applied to ionize the items of the atoms of the pathway and create a path of least resistance for an electrosurgical arc. A reduction in the laser power required can be achieved by matching the photon frequency of the laser with the excitation frequency of the environmental gas. In a laparoscopic procedure, the insufflation gas may be used as the environmental gas.

48 Claims, 12 Drawing Sheets

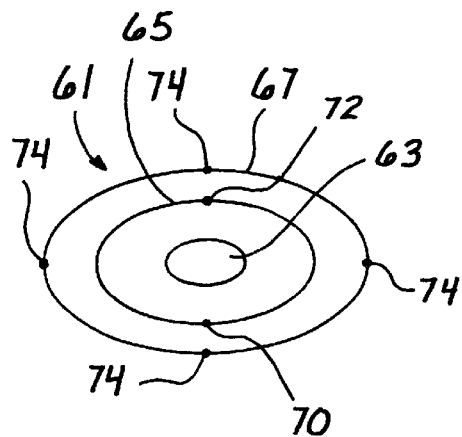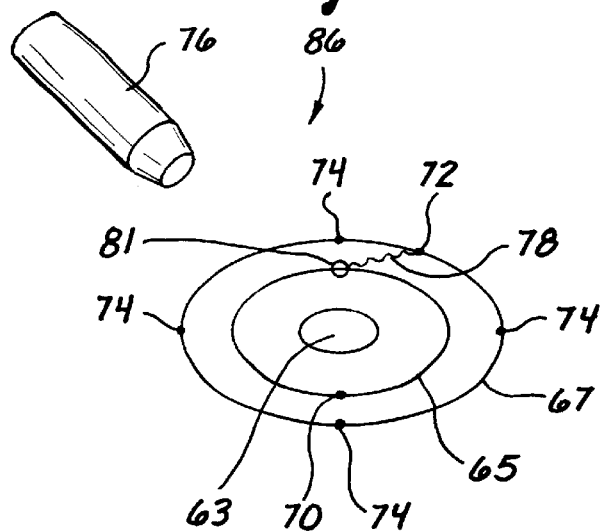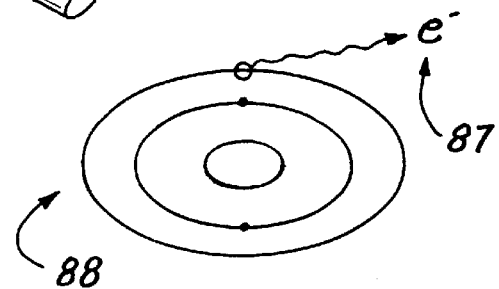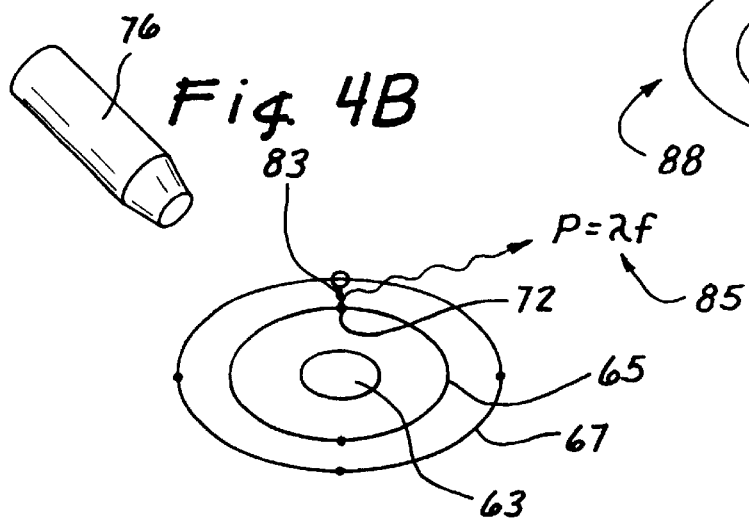

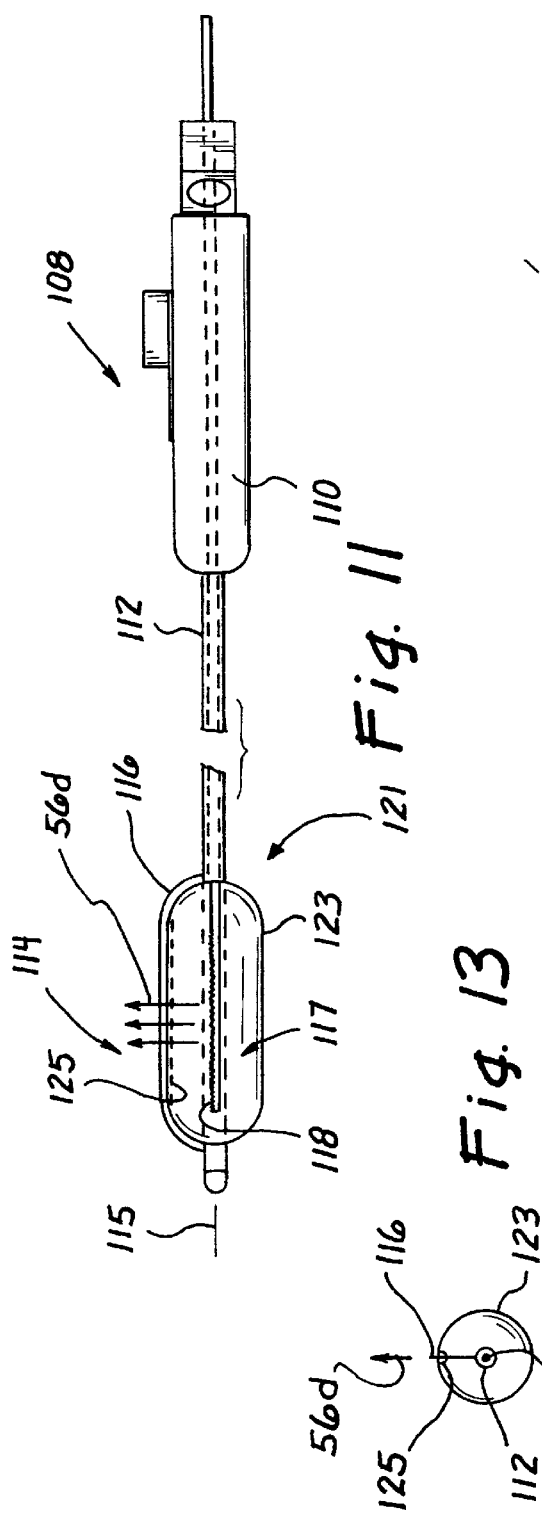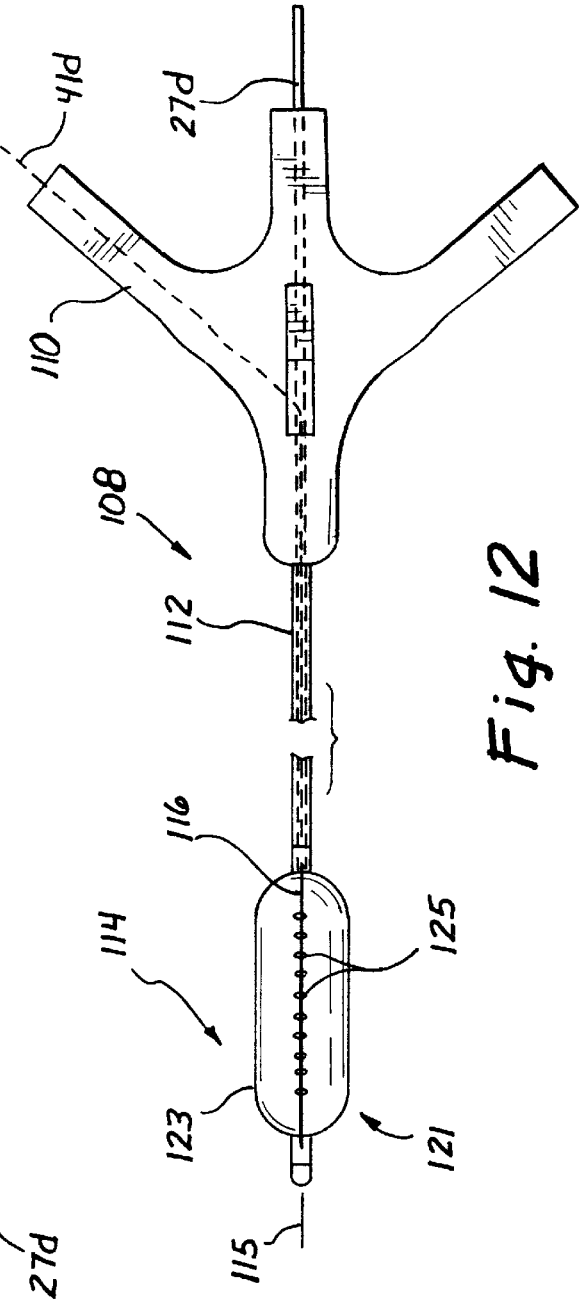
Fig. 11
Fig. 12
Fig. 13

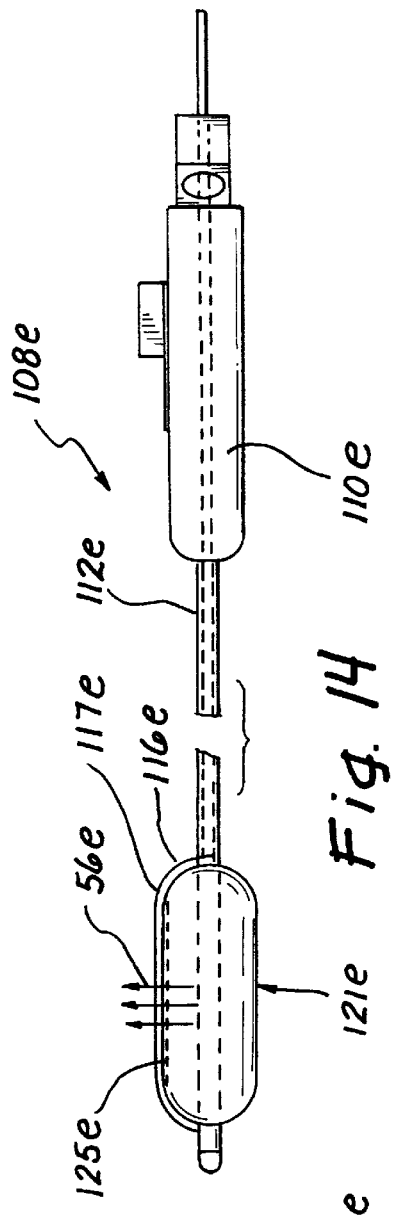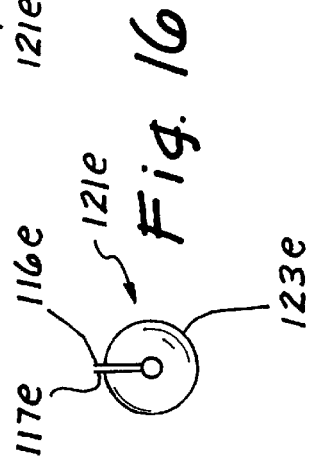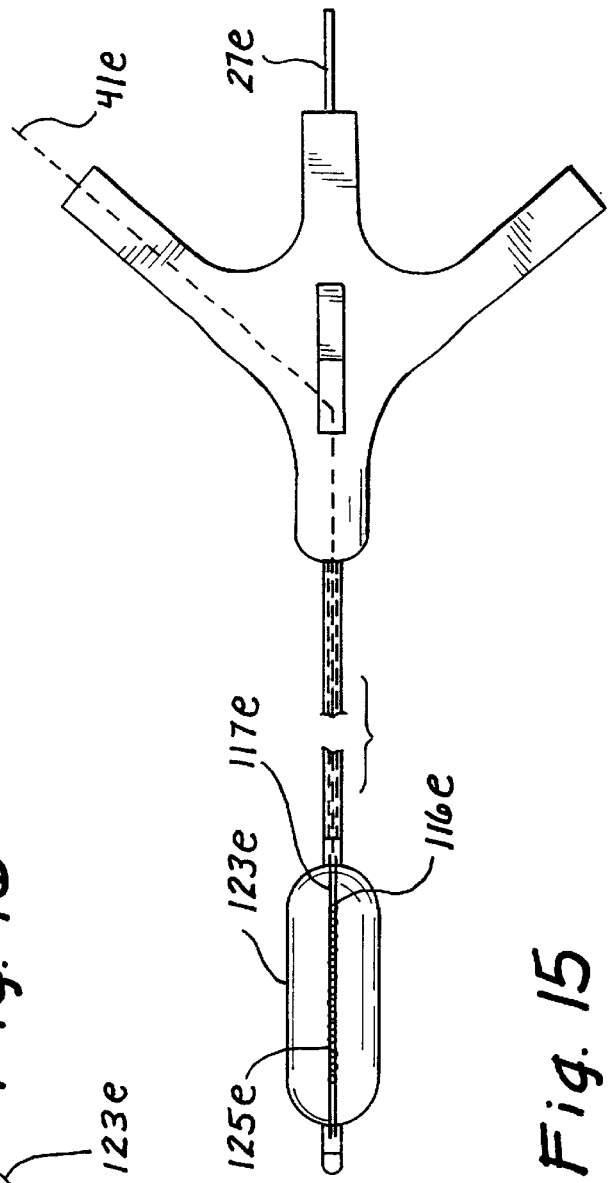

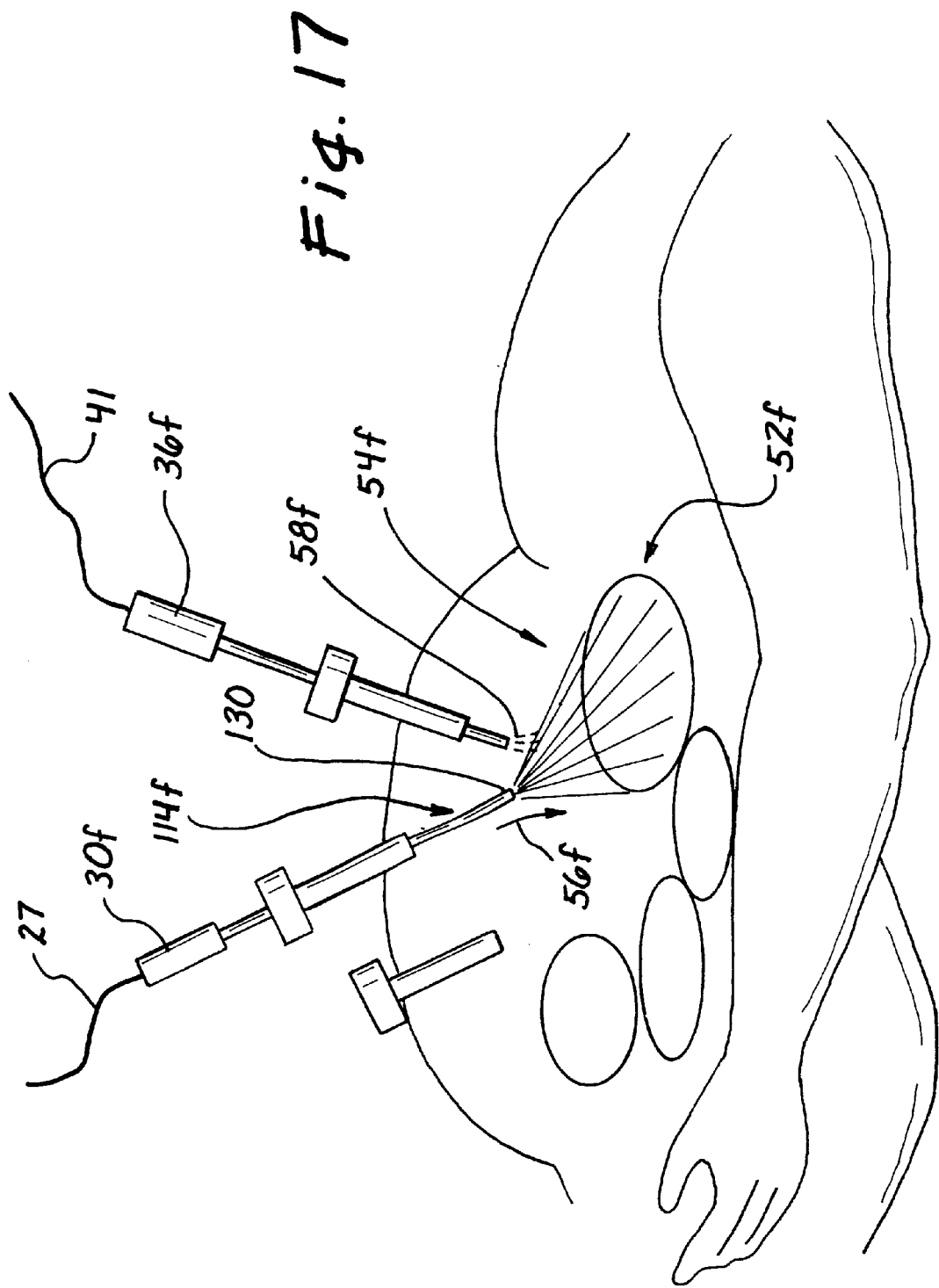

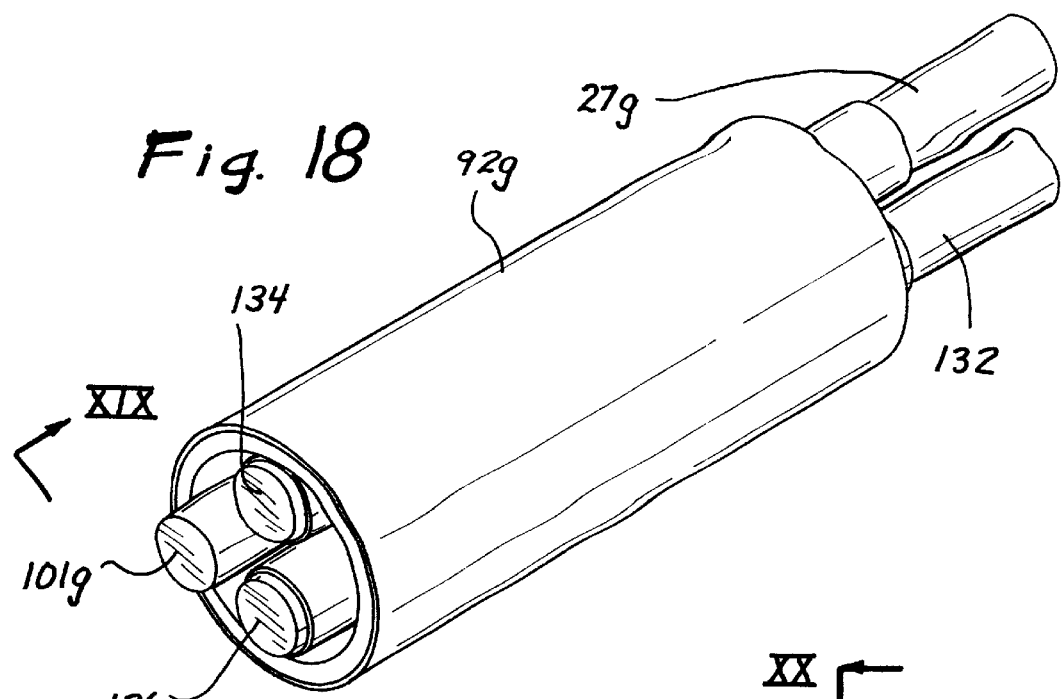
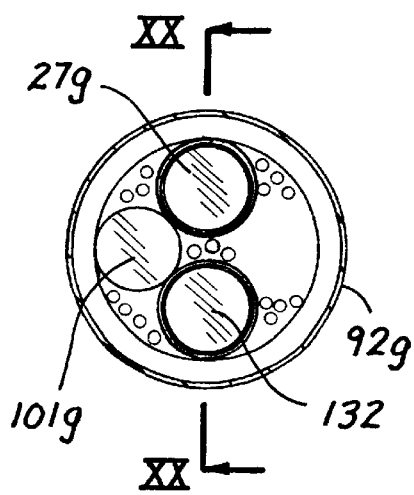
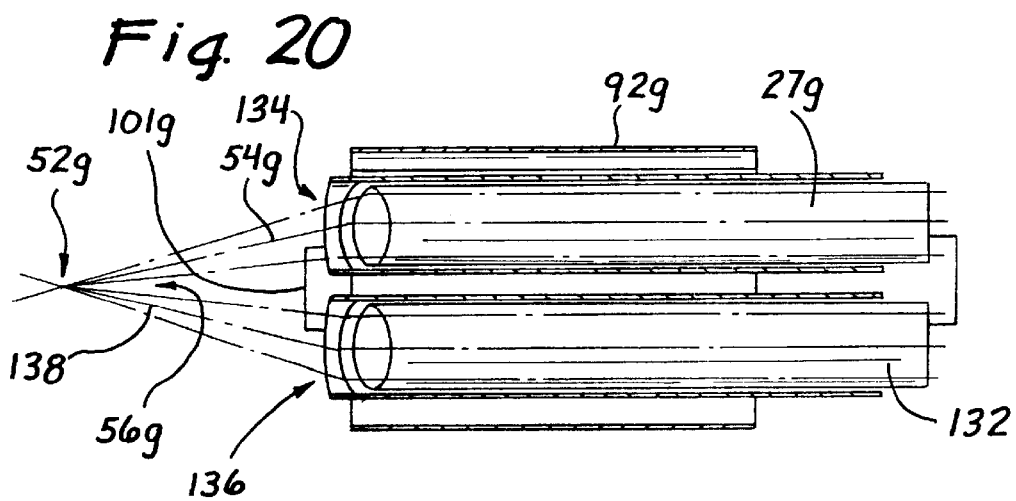

ELECTROSURGERY WITH IMPROVED CONTROL APPARATUS AND METHOD

BACKGROUND OF THE INVENTION

1. Field of the Invention

This invention relates generally to electrosurgery and more specifically to the efficient control of electrosurgical cutting coagulation cautery and fulguration.

2. Discussion of Related Art

The mechanism of electrosurgery is well known in its capability to perform exacting surgical cuts and to provide coagulation, cautery, fulgration and other unique effects. In general, electrosurgery involves the discharge of high voltage at a very high frequency, typically in the form of a spark or arc. However, as with any electrical spark discharge, control is always an issue. Without oversimplifying environment effects, it generally is well known that electricity tends to follow the course of least resistance. Unfortunately this tendency works against the need of a surgeon to have absolute control of an electrosurgical discharge, for example when he is attempting to make a precise surgical incision in very tight quarters, as is the case in laparoscopic procedures.

Failure to achieve this control can cause inadvertent discharge of the electrosurgical spark to an undesirable location. For example, if a metal grasper or clamp is holding a portion of tissue, the electrical spark may discharge to the grasper or clamp rather than overcome a smaller gap to the target tissue. This inadvertent discharge is even more probable realizing that a small gap between target tissue and the electrode is important to achieve an optimal electrosurgical effect.

The designers of electrosurgical generators have produced complex high frequency wave forms and blends of such wave forms, as well as sophisticated feedback and patient monitoring systems to achieve the present level of safety and efficacy. However, there is always the potential for accidental discharge and ancillary damage, particularly when electricity is provided in an open environment. In comparison, to electrical current flows in a wire, electrosurgical discharge by way of an arc has not been particularly controllable. Certainly, a device and method adapted to control and direct an arc of electrosurgical energy would be particularly beneficial.

It is appreciated in U.S. Pat. No. 5,509,916, that a laser can be used to establish an ionized conductive pathway for electrosurgery. The laser ionizes the molecules of air along the laser beam, thereby establishing a path of least resistance leading to an operative site. An electrosurgical spark or arc will follow this path of least resistance, ultimately producing an electrosurgical effect at the operative site. Thus, the laser effectively establishes a means for controlling the electrosurgical arc, thereby avoiding an inadvertent or misdirected discharge.

While this system may work well in air, such a gas may neither be available nor desired in an electrosurgical environment. For example, lasing air would not be available in a laparoscopic environment if carbon dioxide were used as an insufflation gas. Furthermore, complete ionization of (rather than mere excitation) environmental air by a laser may not maximize the efficiency of the laser in establishing a pathway of least resistance.

SUMMARY OF THE INVENTION

In accordance with the present invention, a device and method is disclosed for initiating, directing, and maintaining an electrosurgical discharge in a highly controlled manner. A virtual wire is created which substantially avoids inadvertent and misplaced discharge of the electrosurgical energy. In one aspect, the present invention provides for an environment of gas molecules to be merely excited by a low-power laser beam to create a well-defined path to a precise target. An electrosurgical generator is then provided with sufficient power to fully ionize the excited molecules, thereby creating a path of least resistance to the operative site.

In a preferred embodiment, the device may use the ambient gas of a laparoscopic environment, namely carbon dioxide, and a low powered laser to direct and control an electrosurgical instrument discharge. In an alternate embodiment, the electrosurgical instrument may supply the environmental gas as well as the laser beam. The gas stream and/or the laser beam may be scanned, pulsed, defocused, or otherwise varied to provide a variety of electrosurgical effects.

In order to maximize the efficiency of the system, the laser can be provided with power only sufficient to energize the atoms of the environmental gas. Once these energized atoms have established the pathway to the operative site, energy from the electrosurgical generator can be used to fully ionize the excited molecules to define the path of least resistance.

The present invention can also be used in an environment where air is neither available nor desired. For example in laparoscopic surgery, the insufflation gas, such as carbon dioxide, can provide the environmental gas and can be lased to define the pathway.

Further efficiencies can be generated by providing a laser beam at a frequency depended upon the excitation frequency of the environmental gas. Thus, a carbon dioxide gas discharge laser can most efficiently be used to excite carbon dioxide molecules, for example, in a laparoscopic electrosurgical procedure.

In one aspect, the invention includes an electrosurgical apparatus which is adapted to perform electrosurgery at an operative site on a patient. The apparatus includes a source of shielding gas that provides gas molecules having properties for being energized at a particular frequency to an excited state. A first delivery apparatus is coupled to this source of gas and adapted to deliver the gas molecules in the proximity with the operative site. A laser is adapted to produce a laser beam providing laser energy at a frequency equal to about an integer multiple of the particular frequency of the environmental gas, and at a power generally sufficient to excite the gas molecules. A second delivery apparatus is coupled to the lasers to deliver the laser beam along a pathway leading toward the operative site. An electrosurgery generator provides electrosurgical power and is coupled by a third delivery apparatus which delivers the electrosurgical power along the pathway toward the operative site. A handpiece including a housing and an elongate probe can be used for one or all of the first, second, and third delivery apparatus. The laser energy is provided in an amount generally insufficient to ionize the gas molecules along the pathway. However, the electrosurgical power is provided in an amount generally sufficient to ionize the gas molecules excited by the laser.

In another aspect of the invention, an electrosurgical method is used to perform electrosurgery at an operative site of a patient. The method includes the step of providing a source of environmental gas molecules having an excitation frequency. These molecules are moved into proximity with the operative site and energized with a laser beam having a frequency equal to about an integer multiple of the excitation frequency of the environmental gas. The laser beam is controlled to provide power sufficient to excite the gas molecules along a pathway leading toward the operative site. Electrosurgical power is delivered along this pathway to the operative site to perform the electrosurgery on the patient. The pathway can be established by one or more and the electrosurgical power can be provided in either a monopolar or bipolar configuration.

In another aspect, the invention includes a laparoscopic method for performing electrosurgery at an operative site in the abdomen of a patient. This method includes the step of insufflating the abdomen with gas molecules having an excitation frequency, exciting the gas molecules with a laser beam having a fundamental frequency or a harmonic thereof equal to about the excitation frequency of the insufflation gas, and delivering electrosurgical energy along the pathway of excited molecules to perform the electrosurgical operation at the operative site. The laser beam can be moved relative to the patient to vary the size and shape of the pathway. Either or both the laser beam and the electrosurgery energy can be pulsed.

In a further aspect of the invention, an electrosurgical method is used to perform laparoscopic electrosurgery at an operative site in the abdominal cavity of a patient. The cavity is initially insufflated with a gas having an excitation frequency. This insufflation gas is then lased at a lasing frequency to form a pathway of excited gas molecules leading toward the operative site. Electrosurgical energy is directed along this pathway to produce an electrosurgical effect on the patient.

In another aspect of the invention, a catheter having a proximal end and a distal end is adapted to perform electrosurgery within a body conduit. The catheter includes an elongate shaft which delivers an environmental gas into the conduit. A laser apparatus includes a light fiber carried by the shaft and adapted to release laser energy into the environmental gas to excite gas molecules along the pathway. An electrosurgical apparatus includes an electrode carried by the shaft and adapted to release electrosurgical energy along the pathway to perform electrosurgery along the body conduit. A balloon can be carried by the shaft and inflated with a gas which is controllably released through a hole in the wall of the balloon. This release provides the environmental gas which is lased to produce the pathway. An associated process includes the steps of inflating the balloon with an inflation gas, releasing a portion of the inflation gas from the balloon, exciting molecules of the inflation gas with laser energy to produce a pathway, and introducing electrosurgical energy into the pathway to perform electrosurgery within the body conduit.

In still a further aspect of the invention, the laser which is used for exciting the gas molecules provides a laser beam which is generated from an active medium having a discharge frequency. The active medium may be a gas or a crystal and may be tunable to vary the discharge frequency.

These and other features and advantages of the present invention will become more apparent with a description of preferred embodiments and reference to the associated drawings.

DESCRIPTION OF THE DRAWINGS

FIG. 3 is a schematic view of a typical atom;

FIG. 4A is in a schematic view of the atom being excited;

FIG. 4B is a schematic view of an excited atom giving up energy in the form of a photon.

FIG. 4C is a schematic view of the excited atom being ionized;

FIG. 11–FIG. 20 illustrates a catheter of the present invention including a balloon providing for the controlled release of an inflation gas to provide the environmental gas for the present invention;

FIG. 11 is a side elevation view of one embodiment of a balloon catheter;

FIG. 12 is a top plan view of the embodiment of FIG. 11;

FIG. 13 is an end elevation view of the embodiment of FIG. 11;

FIG. 14 is a side elevation view of a further embodiment of a balloon catheter adapted for use in a bipolar configuration;

FIG. 15 is a top plan view of the embodiment of FIG. 14;

FIG. 16 is an end elevation view of the embodiment of FIG. 14;

FIG. 17 is a side elevation view similar to FIG. 2 and showing a laser beam being defocused to facilitate electrosurgical coagulation;

FIG. 18 is a perspective view of an embodiment including two lasers with beams that converge toward the operative site of the patient;

FIG. 19 is an end view taken along lines XIX–XIY of FIG. 18; and

FIG. 20 is an axial cross section view taken along lines XX—XX of FIG. 19.

DESCRIPTION OF PREFERRED EMBODIMENTS AND BEST MODE OF THE INVENTION

Figure 1:
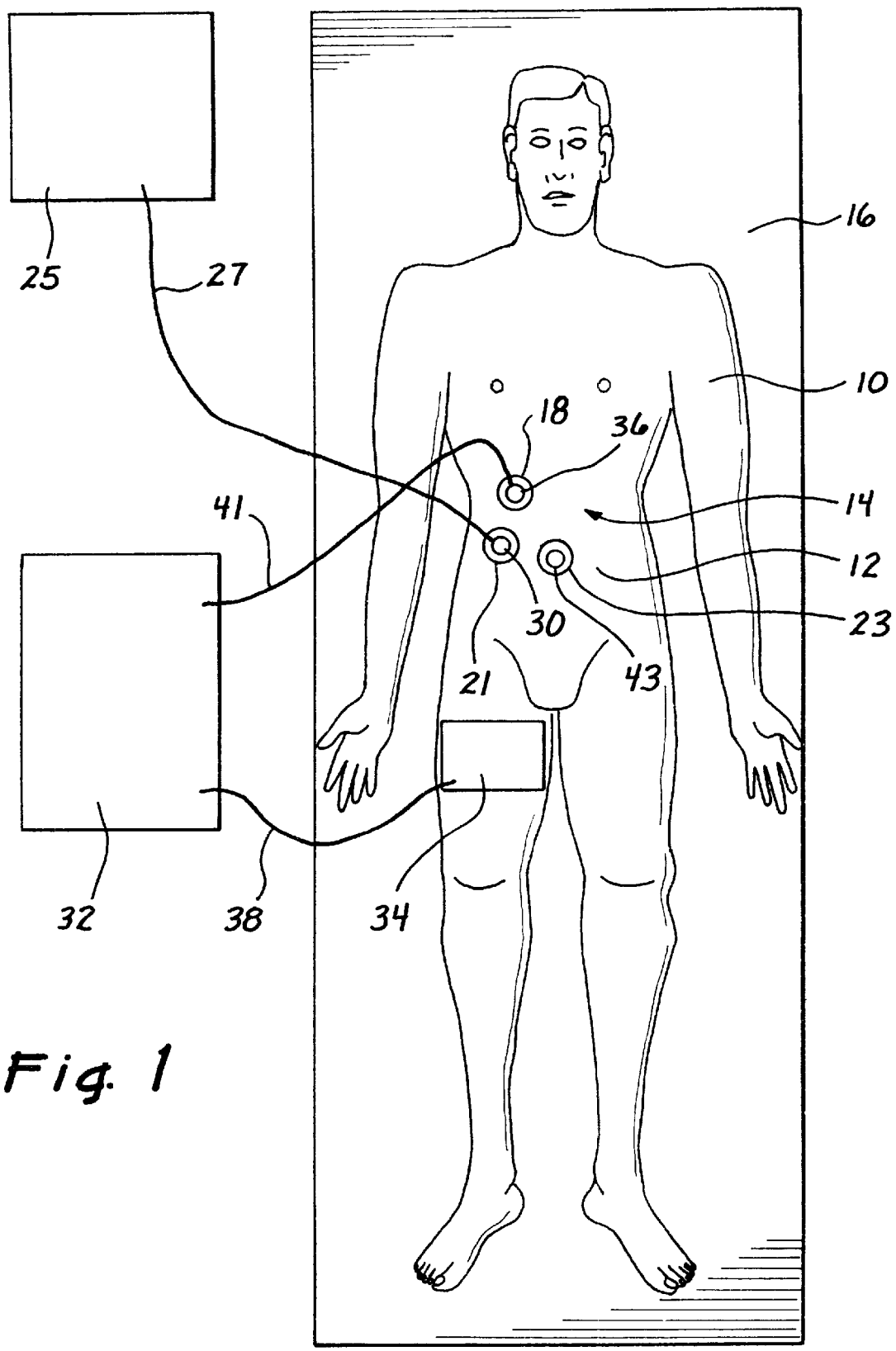
FIG. 1 is a top plan view illustrating a patient disposed on an operating table and prepared for laparoscopic surgery.

A patient is illustrated in FIG. 1 and designated generally by the reference numeral 10. The patient 10 has an abdominal wall 12 which defines an interior abdominal cavity of 14. In this view, the patient 10 is disposed on an operating table 16 and is prepared for laparoscopic surgery which is performed through the abdominal wall 12 within the abdominal cavity 14.

A laparoscopic procedure is facilitated by a plurality of elongate trocars 18, 21, and 23, which are inserted through the abdominal wall and into the abdominal cavity 14. Various instruments can be inserted into and removed from the trocars 18, 21, and 23 to facilitate a particular operative procedure within the abdominal cavity 14.

In FIG. 1, the patient 10 is prepared for electrosurgery in a laparoscopic procedure. A laser 25 is provided and connected through an optical fiber 27 to a laser probe 30 extending through the trocar 21. In like manner, an electrosurgical generator 32 is provided in a monopolar configuration with a grounding plate 34 and an electrosurgery handpiece 36. The grounding plate 34 is connected to the generator 32 through a lead 38, and provides a large area of electrical contact with the patient 10. The handpiece 36 is connected to the generator through a lead 41 and can be inserted through the trocar 18 into the abdominal cavity 14. Other instruments useful in this procedure might include a laparoscope 43 which might typically be inserted through the trocar 23 to provide for illumination and visualization within the cavity 14.

Figure 2:
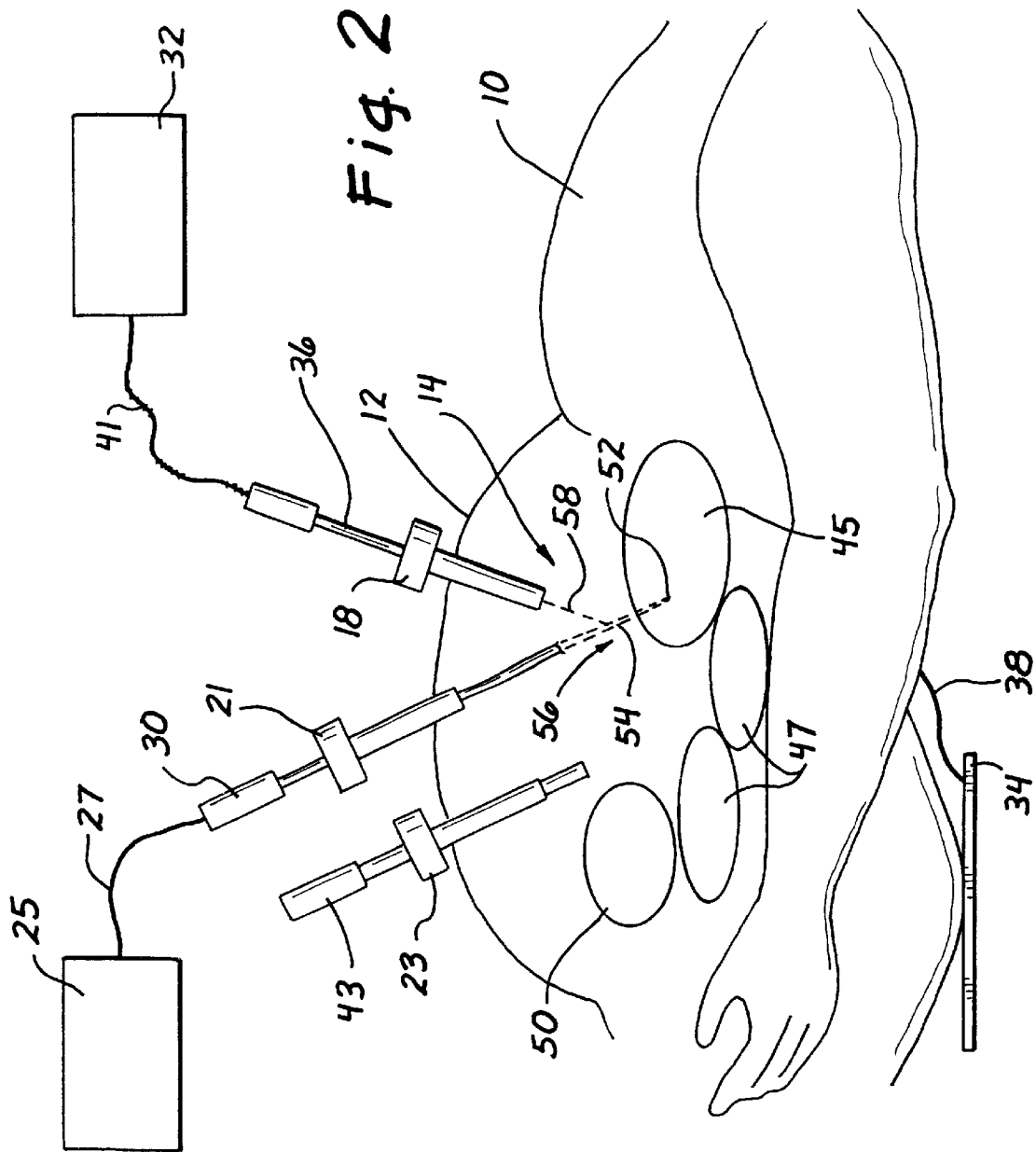
FIG. 2 is a side elevation view of the patient showing interior regions of the abdominal cavity during the laparoscopic procedure.

This arrangement of trocars and instruments is best illustrated in the side elevation view of FIG. 2. In this figure, the abdominal cavity 14 is illustrated to include various organs such as a stomach 45, kidneys 47, and bladder 50. In the illustrated procedure, electrosurgery is being performed at an operative site 52 on the stomach 45.

In accordance with a preferred method of the present invention, the abdominal cavity 14 is initially inflated or insufflated with a gas such as carbon dioxide. This insufflation distends the abdominal wall 12 thereby increasing the volume of the working area within the abdominal cavity 14. After the cavity 14 has been insufflated, the laser probe 30 can be inserted through the trocar 21 and activated to direct a laser beam 54 toward the operative site 52.

In a manner described in detail below, the laser beam 54 energies the molecules of the insufflation gas to create a pathway 56 leading toward the operative site 52. Once this pathway 56 is established, the electrosurgical generator 32 can be activated to produce an electrosurgical potential between the handpiece 36 and the grounding pad 34. This potential will produce a spark or arc 58 which is intended to produce an electrosurgical effect at the operative site 52. Control of this spark or arc 58 is maintained by introducing the arc 58 in proximity to the pathway 56 of excited molecules.

In a preferred method, electrosurgical potential ionizes the excited molecules along the pathway 56 to create a path of least resistance leading toward the operative site 52. Following this pathway 56, now defined by ionized molecules, the arc 58 can create the desired electrosurgical effect at the operative site 52.

This procedure, including the steps of lasing the insufflation gas to excite molecules along a pathway, and then ionizing the excited molecules can best be understood on the atomic level. In FIG. 3, an atom 61 is illustrated schematically to include a nucleus 63 and two electron orbits or shells 65 and 67. Two electrons 720 and 72 are normally present in the inner most or first shell 65 while four electrons 74 are typically present in the second shell 67, the outer most shell in this particular atom. The atoms associated with the various elements in the periodic table differ primarily in the makeup of the nucleus 63, as well as the number of shells, such as the shells 65, 70, and number of electrons, such as the electrons 70, 72 and 74.

Of particular interest to the present invention is the nature of the electrons 70, 72, 74, when they are exposed to an energy source, such as an electrical probe 76. Initially it is noted that in each of the shells 65 and 67, the associated electrons have different energy levels. These energy levels are lowest at the inner shell 65 and highest at the outer shell 67.

In response to the electrical field produced by the electrode 76, the electrons, such as the electron 72, become energized. As the energy level of the electron 72 increases, it moves from the lower energy shell 65 to the higher energy shell 67 as shown by an arrow 78 in FIG. 4A. As the electron 72 moves outwardly, it leaves an electron void or hole 81 in the first shell 65.

Even in the continued presence of the electrical field and the electrode 76, the electron 72 in the outer shell 67 is unstable particularly with the electron hole 81 present in the lower energy shell 65. As a consequence, the electron 72 will tend to fall back into the inner shell 65 as illustrated by the arrow 83 in FIG. 4b. As the electron 72 moves from a higher energy level in the shell 67 to a lower energy level in the shell 65, the difference in energy is released as a photon 85 For purposes of future discussion, note that for a particular atom, the photon released in this process has a known energy level equal to the product of its frequency (f) and its wavelength ($\lambda$).

In very basic terms, this describes the operation of a laser wherein the photons are collected and collimated into a laser beam such as the beam 54 (FIG. 2). In this process it will be noted in particular that the energized electrons move between the shells 65, 67 of the atom 61. As a result, the number of electrons associated with the atom does not change. The atom is merely excited, not ionized. This excited atom is designated in FIG. 4A by the reference numeral 86.

If additional energy is applied to an already excited atom, as illustrated in FIG. 4C, the energy of the electron, such as the electron 72 may exceed that necessary to maintain it in the outer shell 67. Under these circumstances, the electron 72 may be separated from the atom 61, as a free electron 87. This leaves an ionized atom 88 in a charged state. Importantly, the free electrons which result from this ionization, change the properties of the pathway 56 (FIG. 2). What was heretofore merely a pathway of excited atoms is now a pathway of ionized atoms which for the first time offers a path of least resistance for the electrical arc (FIG. 2).

Figure 5:
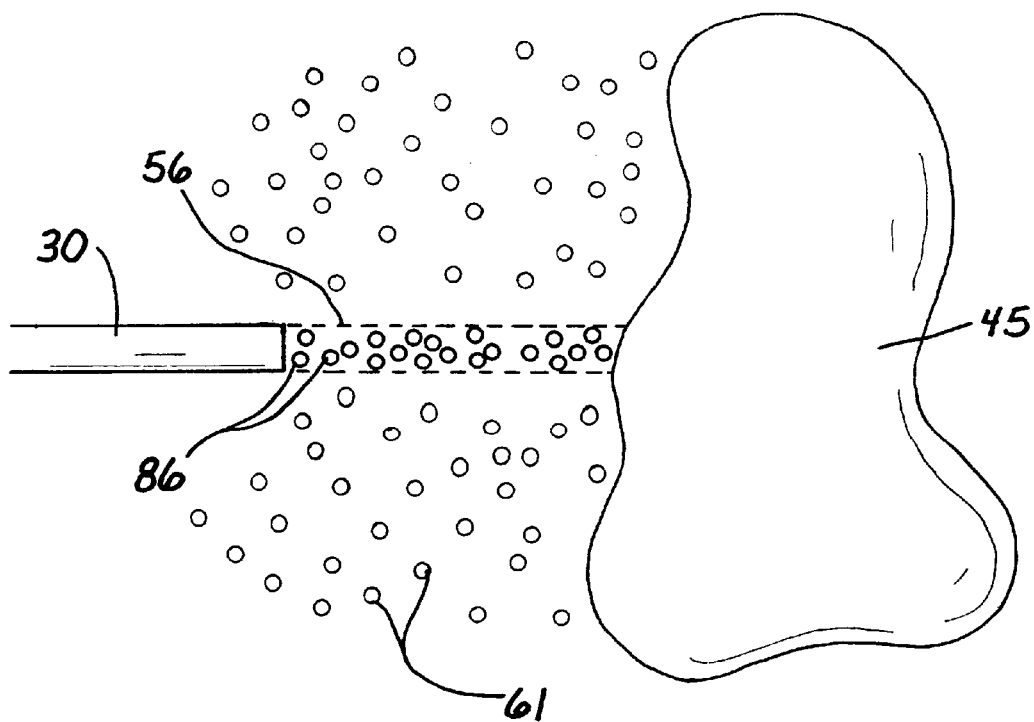
FIG. 5 is a schematic view of a process for creating a pathway of excited molecules.
Figure 6:
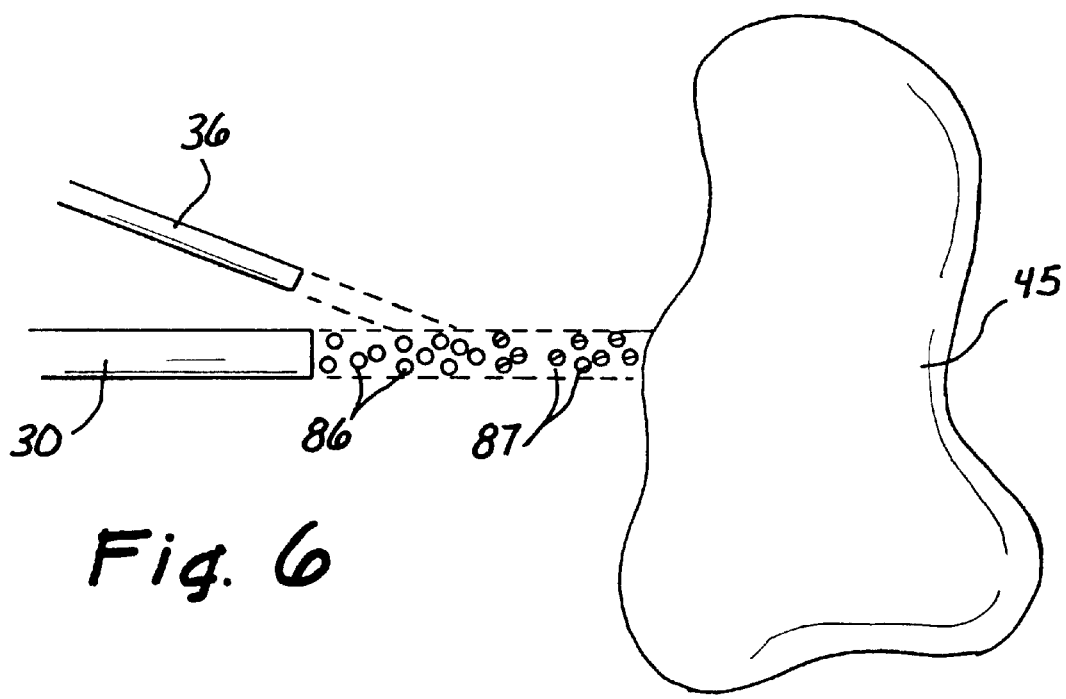
FIG. 6 is a schematic view of a process for ionizing the excited molecules in the pathway.

Given the distinctions between an energized atom and an ionized atom, it can now be appreciated that the pathway 56 illustrated in FIG. 2 and FIG. 5 can initially be established merely by the excited atoms 86. Although these excited atoms 86 will not produce a path of least resistance, they nevertheless establishes a pathway of atoms which have already reached an excited state. Under these circumstances, the electrosurgical handpiece 36 can provide the remaining energy necessary to ionize the excited molecules as illustrated in FIG. 4C. The resulting release of free electrons (shown by the arrow 87 in FIG. 4C) makes the pathway 56 a path of least resistance for subsequent delivery of the arc 58 toward the operative site 52.

In the past, electrosurgery has been performed in open procedures using a laser to fully ionize air along a pathway leading to an operative site. Relying on a laser to produce a fully ionized pathway of least resistance has necessarily required a very high magnitude of laser power. Now, in accordance with this invention, the laser is only required to produce a pathway of excited atoms rather than a pathway of fully ionized atoms. Although the pathway 56 resulting from this laser application does not define a path of least resistance, nevertheless a path to the operative site is defined by the excited atoms 86. These atoms are most susceptible to the further application of energy to create ionized atoms 88 and free electrons 87, thereby resulting in an ionized pathway of least resistance.

It is of particular interest to the present invention to contemplate the amount of energy, and particularly the frequency of the energy, used to energize the atom 61. It has been noted that the amount of energy required to displace an electron between atom shells varies with the particular atom involved. Thus, an atom of oxygen would require a different level of excitation energy then would an atom of carbon, for example. In addition, the amount of excitation power required is reduced when it is applied at a frequency which is dependent upon the excitation frequency of a particular atom. Importantly, when the excitation power is applied at a frequency dependent upon the excitation frequency of the atom, the amount of power required is reduced.

The excitation frequency in this case is the same as the frequency previously discussed with reference to the energy of the photon 85 (FIG. 4B). Energy applied at this excitation frequency, or a harmonic thereof, requires less power to create the excited atom, such as the atom 86. Thus, if the photon frequency of the laser 86 is chosen to be the fundamental frequency (or the harmonic thereof) of the excitation frequency associated with the environmental gas, the power required for excitation can be greatly reduced. The same power advantages can be achieved by choosing the laser 76 with a photon frequency equal to the excitation frequency or any integer multiple or divisor thereof.

Of course there are several types of lasers including gas discharge lasers as well as crystal and diode lasers. Each laser has its own photon frequency which can be chosen relative to the excitation frequency of the environmental gas being used. Of course the gas discharged lasers are easiest to contemplate with the present invention, as it is only necessary to choose the particular laser having a discharge gas which is the same as that of the environmental gas used in the electrosurgical process. In some cases, the environmental gas will dictate the choice of the laser, while in other cases, the laser will dictate the choice of the environmental gas.

In a laparoscopic surgery environment, carbon dioxide is most commonly used as an insufflation gas. This gas necessarily defines the environmental gas for an electrosurgical laparoscopic procedure. The best choice for a laser under these circumstances would be a carbon dioxide discharge laser. This laser would require the least power to create the pathway of excited atoms in an insufflated laparoscopic procedure using carbon dioxide as the insulation gas.

Figure 7:
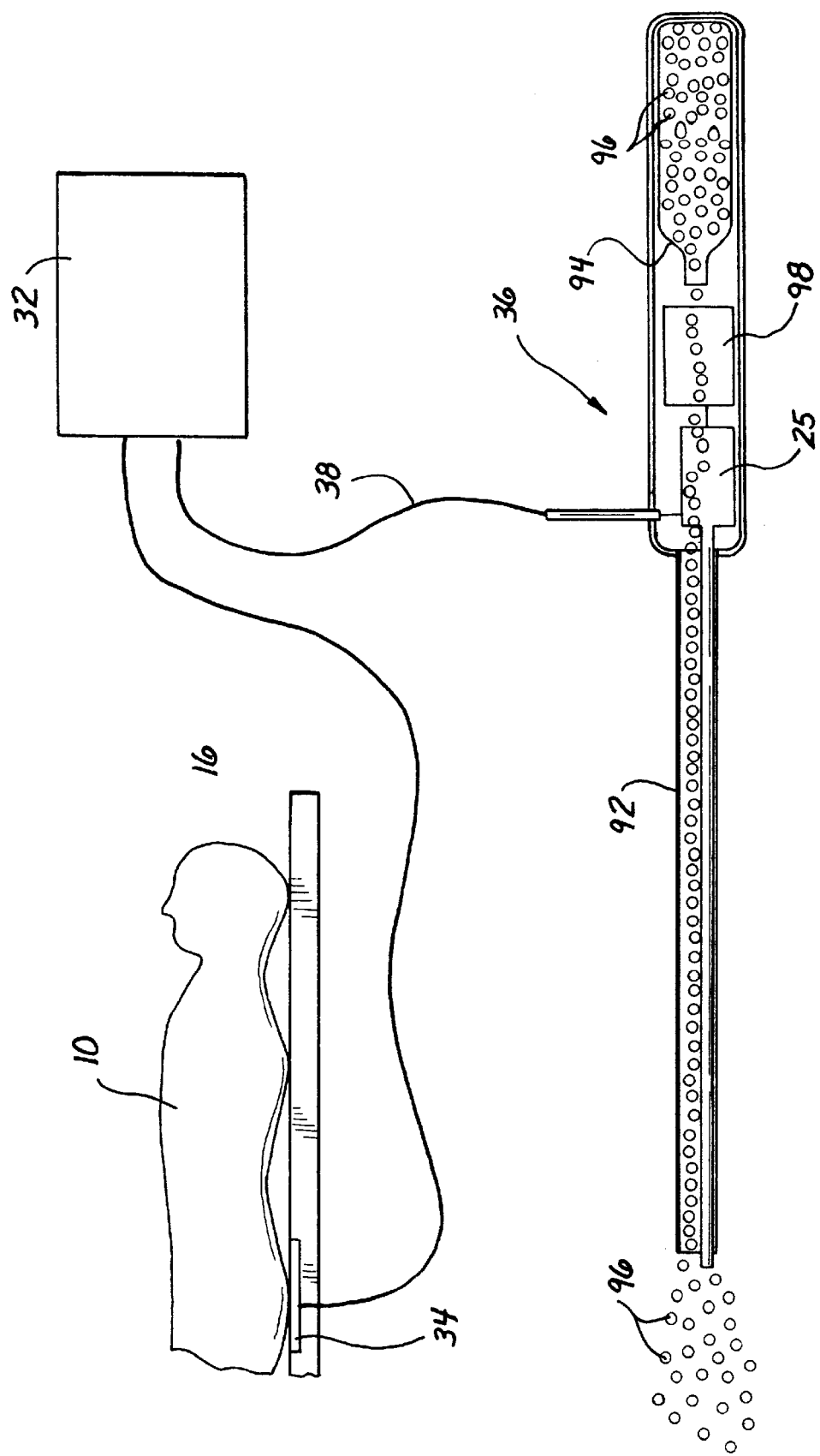
FIG. 7 is an axial cross section view illustrating a handpiece having a housing and probe and being adapted for use in a monopolar electrosurgery procedure.

Given the low power requirements for the laser 25 in the present invention, a preferred embodiment for the handpiece 36 might be that illustrated in FIG. 7. In this case, the handpiece 36 includes a housing 90 communicating with an elongate probe 92. A gas cartridge 94 can be carried by the housing 90 and adapted to release gas molecules 96 into the housing 90 and through the probe 92. These molecules 96 would provide the environmental gas in those procedures not otherwise providing an insufflation gas. The laser 25 and associated batteries 98 could also be carried in the housing 90. Activation of the laser 25 through the optical fiber 27 would energize the atoms associated with the gas molecules 96 to create the energized pathway.

The handpiece 36 could be coupled through the lead 41 to the electrosurgical generator 32. The generator 32, in a monopolar configuration would also be coupled through the lead 38 to the groundplate 34 disposed between the patient 10 and the operating table 16. Activation of the electrosurgical generator 32 would produce the electrosurgical power necessary to ionize the atoms of excited gas in the pathway 56. As previously discussed, this would create the path of less resistance for subsequent electrosurgical arcing to the operative site 52 on the patient 10.

Figure 8:
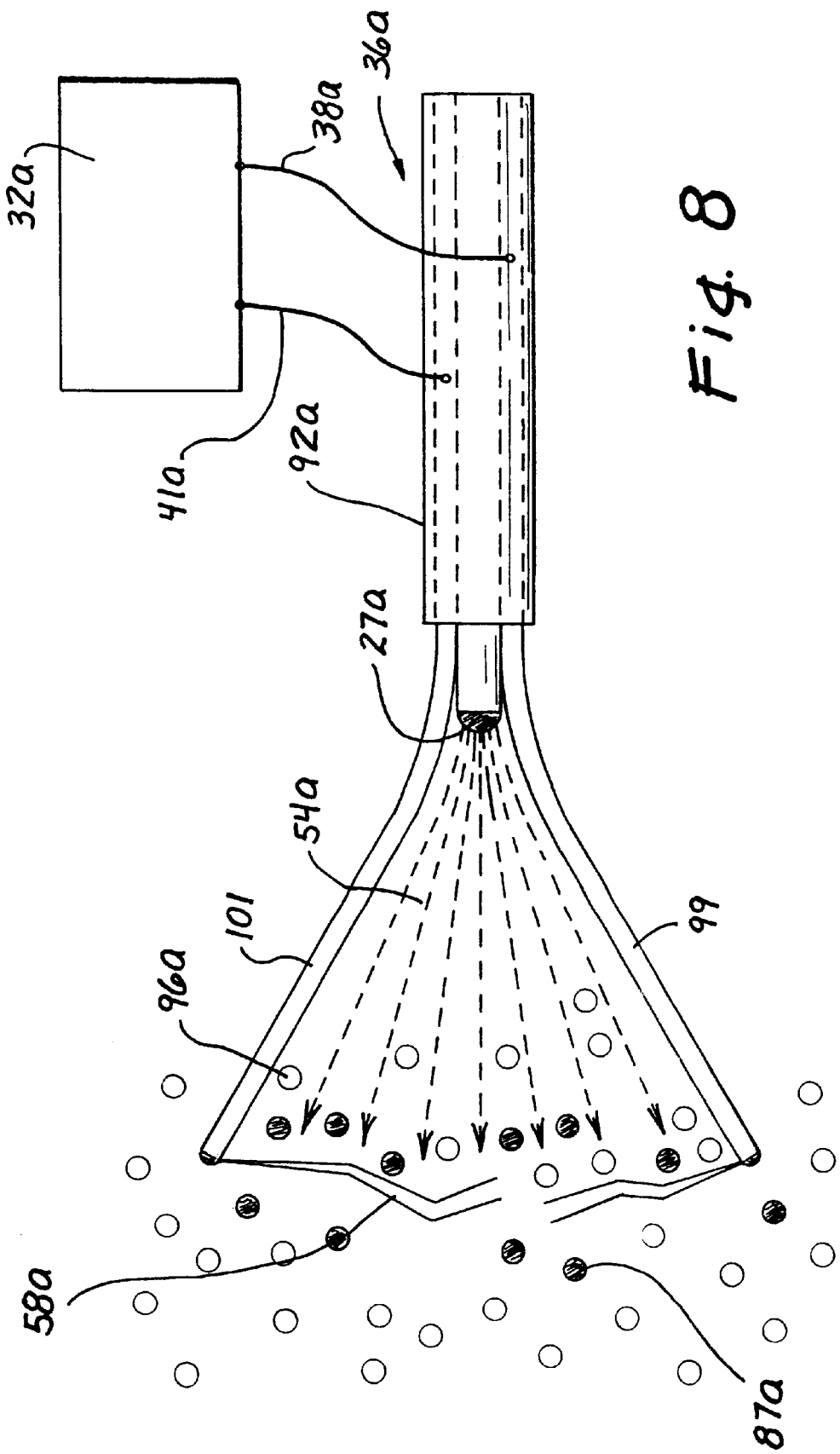
FIG. 8 is a side elevation view of a handpiece adapted for use in a bipolar electrosurgery procedure.

In a bipolar configuration, the handpiece 36 might be constructed as illustrated in FIG. 8. In this embodiment, elements of structure similar to those previously discussed are designated with the same reference numeral followed by the lowercase letter "a." Thus, the handpiece 36 is shown with the probe 92a including the optical fiber 27a, and the gas molecules 96a are energized by the laser beam 54a. In this bipolar embodiment, the probe 92a includes two electrodes 99 and 101 which are connected respectively to the leads 38a and 41a of the electrosurgical generator 32a. In this embodiment, the spark or arc 58a will jump between the electrodes 99 and 101 along the pathway 56 of energized free electrons 87a.

Figure 9:
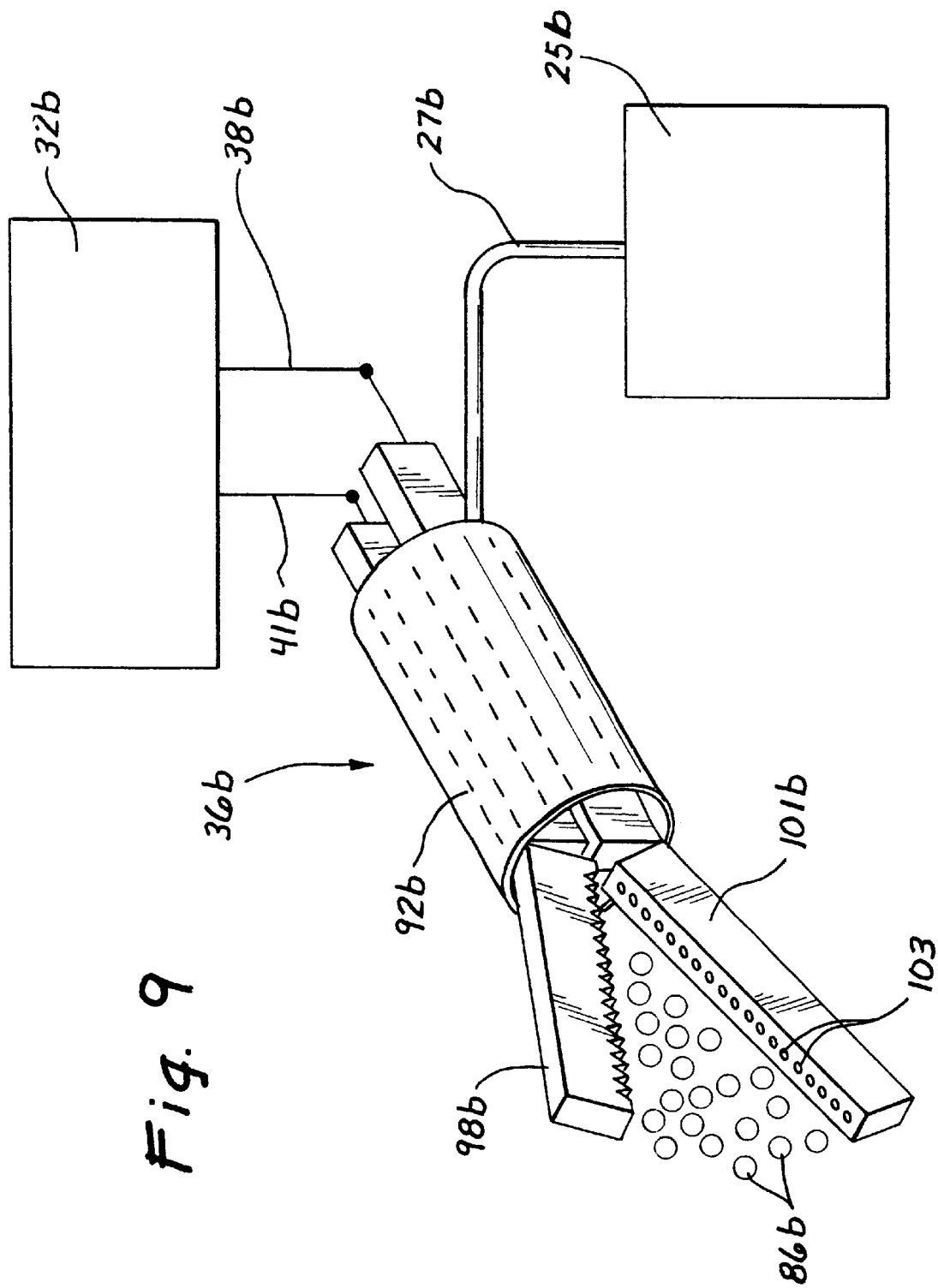
FIG. 9 is a perspective view of a handpiece including jaws.

Another embodiment for the hand piece 36 is illustrated in FIG. 9 wherein elements of structure similar to those previously disclosed on designated with the same reference followed by the lowercase letter "b." In this embodiment, the probe 92b includes the two electrodes 99b and 101b in a bipolar configuration, with the electrode 101b being provided with fiberoptic apertures 103. Operation of this embodiment is similar to that of FIG. 8 in that the environmental gases can be carried through the probe 92b to the vicinity of the electrodes 99b and 101b. The laser 25b can be coupled through the optical fiber 27b to the fiber apertures 103 in order to excite the molecules of environmental gas. Electrosurgical power can then be provided by the generator 32b and through the leads 38b and 41b to the electrodes 101b and 99b, respectively. This will produce the desired ionization of the excited atoms 86b and facilitate arcing along a controlled pathway between the electrodes 98b and 101b.

Figure 10:
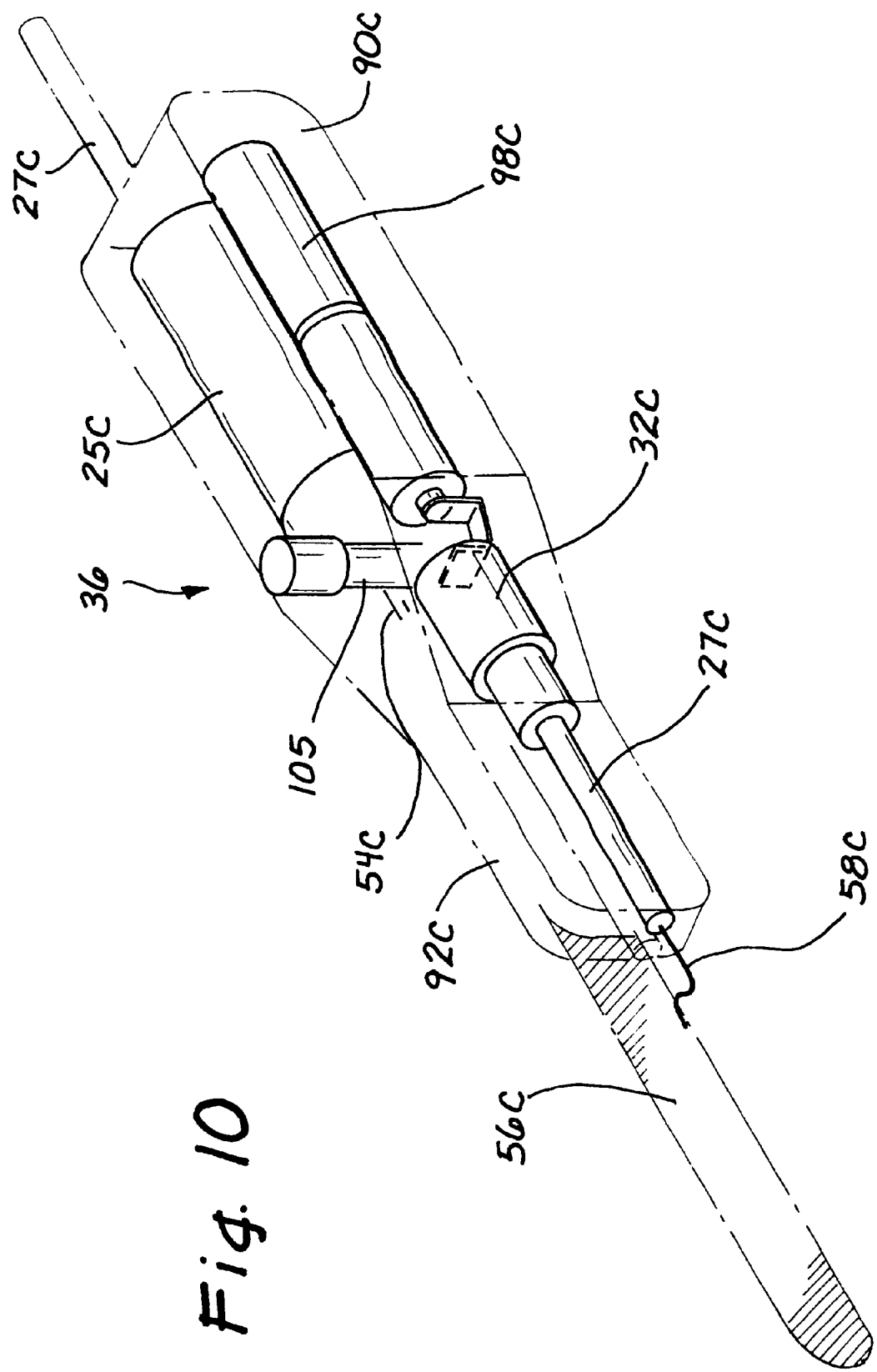
FIG. 10 is a perspective view of a handpiece having a blade configuration.

FIG. 10 illustrates an embodiment of the handpiece 36 which is adapted to function as a laser knife or scalpel. In this embodiment, elements of structure similar to those previously discussed will be designated with the same reference numerals followed by the lowercase letter "c." In FIG. 10, the handpiece 36 is illustrated to be completely self-contained and with powering both the laser 25c and the electrosurgery generator 32c.

In a procedure wherein the environmental gas is provided, for example by an insufflation gas, the laser 25c can initially be operated to energize the environmental gas molecules. In this case, the embodiment of FIG. 10 provides for the laser beam 54c to be moveable through an aperture 105 to create the pathway 56c having an elongate and generally planar configuration. By energizing the electrosurgical generator 32c, the electrode 27c is activated to ionize the atoms in the pathway 56c. This facilitates the controlled delivery of the electrosurgical spark or arc 58C along the planar pathway 56c.

A further embodiment of the invention is illustrated in the side elevation view of FIG. 11 where elements of structure similar to those previously disclosed are designated with the same reference numeral followed by the lowercase letter "d." In FIG. 11, the concept of the invention is embodied as a catheter 108 having a hub 110 and a catheter body 112 which extends to a distal end 114 along an axis 115. As best illustrated in the plan view of FIG. 12, the electrosurgical lead 41b from the electrosurgical generator 32 (FIG. 1), and the optical fiber 27d from the laser 25 (FIG. 1), can be introduced into the hub 110 and extended through the catheter body 112. At the distal end 114, the electrosurgical lead 41d can be terminated in an electrode which in a preferred embodiment comprises a wire 116.

Also at the distal end 114, the optical fiber 27d can be provided with a distal tip having facets 118, or a refractive index coating selectively removed, to permit the escape of light in a direction desired for the pathway 56d. In the illustrated embodiment, this direction is laterally of the axis 115 as shown by the pathway arrows 56d. In a particular embodiment wherein the environmental gas is already present, the wire electrode 116 and the optical fiber 27d may be all that is required to implement the concept of the present invention. Applying laser energy through the optical fiber 27d will excite the atoms of the environmental gas creating the pathway 56d in the direction dictated for example by the facets 118. Activating the wire electrode 116 will then cause electrosurgical energy to ionize the pathway 56d and create the desired electrosurgical effect.

A balloon 121 can also be provided at the distal end 114 of the catheter 108 to perform typical catheter balloon functions. In the illustrated embodiment, the balloon 121 has an inflatable wall 123 which includes portions that define a series of perforations 125. The balloon 121 may be centered on the catheter body 112 with the faceted distal tip 117 of the optical fiber 27d disposed within the balloon 121, for example near the axis 115. In this embodiment, the wire electrode 116 is preferably disposed along the outer surface of the balloon wall 123.

In operation, gas can be introduced through the hub 110 and along the catheter body 112 to inflate the balloon 121. As the balloon 121 is inflated, the inflation gas is permitted to leak through the perforations 125 into the environment surrounding the balloon 121. At this point, the laser 25 (FIG. 1) can be activated to direct laser energy along the optical fiber 27d and to energize the atoms of the environmental gas along the pathway 56d. In the illustrated embodiment, this pathway 56D will extend from within the balloon 121, through the inflation gas within the balloon 121, outwardly through the perforations 125, and through the environmental gas toward the operative site. Upon activation of the wire electrode 116, electrosurgical power will follow the pathway 56a to create the electrosurgical effect.

The embodiment of a catheter, such as the catheter 108, can be a particular advantage where the electrosurgical effect is desired within a body conduit, such as the ureter. In such an embodiment, the addition of the balloon 121 can produce many synergistic effects. For example, the mere inflation of the balloon can carry the electrode wire 116 into closer proximity to the wall of the conduit. And as noted, the gas used to inflate the wall 123 of the balloon 121 can also provide the environmental gas for the electrosurgical procedure. Appropriately perforated, the balloon 121 can be used to release the inflation gas into the environment and in a predetermined direction.

Another catheter embodiment is illustrated in the side view of FIG. 14, the top view of FIG. 15, and the end view of FIG. 16. In these views, elements of structure similar to those previously described are designated with the same reference numeral followed by the lower case letter "e." Thus, the catheter 108e includes the hub 110e and the catheter body 12e. The balloon 121e is also included with its wall 123e and perforations 125e. As in the embodiment of FIG. 11, the electrode wire 116e is disposed along the outer surface of the balloon wall 123. However, in this embodiment, the distal tip 117 of the optical fiber 127e is also carried on the outer surface of the balloon wall 123.

As in the previous embodiment, inflation gas can be introduce into the balloon 121e thereby expanding the wall 123 and carrying the electrode wire 116e and optical fiber distal tip 117 radially outwardly. As before, this inflation gas can be permitted to leak through the perforations 125e into the environment. When the laser fiber 127e is activated, the distal tip 117e will direct laser energy outwardly from the wall 123e of the balloon 121e in order to create the energized pathway 156e. As in the previous case, activation of the electrode wire 116e will follow this pathway 156e toward the operative site.

A further embodiment of the laser probe is illustrated in FIG. 17 which provides a view similar to that of FIG. 2. In FIG. 17, elements of structure similar to those previously disclosed will be designated with the same reference numeral followed by the lower case letter "f." In this embodiment, the probe 30f has a distal end tip that is provided with a lens 130 at its distal end 114f. This lens 130 tends to diverge the laser beam 54f so that the operative site 52f is defined by an area, rather than a point as previously illustrated for the embodiment of FIG. 2. With the laser beam 54f diverging, the pathway 56f of excited atoms also expands as it approaches the area of the operative site 52f. When the electrosurgical handpiece 36f is activated, the spark or arc 58f will be randomly directed within the area of the operative site 52f. This can be of particular advantage when the desired electrosurgical effect is to cauterize or coagulate over a wide area of the operative site 52f.

A further embodiment of the handpiece 36 is illustrated in FIGS. 18–20 wherein elements of structure similar to those previously discussed are designated with the same reference numeral followed by the lower case "g." Thus the handpiece 36g includes the probe 92g containing at least the optical fiber 27g and the electrosurgical electrode 101g. In the illustrated embodiment, the probe 92g also contains a second optical fiber 132. In this case, the two optical fibers 27g and 132 are distally terminated at lenses 134 and 136, respectively. The lens 134 associated with the fiber 27 causes the laser beam 54g to converge as illustrated. Similarly, the lens 136 associated with the fiber 132 causes a laser beam 138 to converge. Importantly, these two laser beams 54g and 138 can also be converged toward the operative site 52. This embodiment offers the advantage of providing increased laser power for development of the pathway 56g. Even with this increased power, the pathway 56g can be controlled to converge the electrosurgical energy toward the operative site 52g.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims

What is claimed is:

1. An electrosurgical apparatus adapted to perform electrosurgery through a handpiece at an operative site on a patient, comprising:

a source of environmental gas providing gas molecules having properties for being energized at a particular frequency to an excited state;

first delivery apparatus disposed in the handpiece and coupled to the source of gas, the first delivery apparatus being adapted to deliver the gas molecules into proximity with the operative site;

a laser disposed in the hand piece and adapted to produce a laser beam providing laser energy at a frequency equal to about an integer multiple of the particular frequency of the environmental gas, and at a power generally sufficient to excite but not ionize the gas molecules;

second delivery apparatus coupled to the laser in the handpiece for delivering the laser beam along a pathway leading toward the operative site;

an electrosurgery generator providing electrosurgical power; and third delivery apparatus disposed in the handpiece and coupled to the electrosurgery generator, the third delivery apparatus being adapted to deliver the electrosurgical power along the pathway toward the operative site.

2. The electrosurgical apparatus recited in claim 1, wherein the laser energy is provided in an amount generally insufficient to ionize the gas molecules along the pathway.

3. The electrosurgical apparatus recited in claim 2, wherein the electrosurgical power is provided in an amount generally sufficient to ionize the gas molecules excited by the laser.

4. The electrosurgical apparatus recited in claim 1, wherein:

the source of gas provides molecules of a first gas; and the laser has properties for generating the laser energy in an environment containing molecules of a second gas.

5. The electrosurgical apparatus recited in claim 4, wherein the first gas contains molecules of the second gas.

6. The electrosurgical apparatus recited in claim 4, wherein the first gas and the second gas contain molecules of at least one of carbon dioxide, argon, and helium.

7. The electrosurgical apparatus recited in claim 1 wherein the laser is a first laser and the laser beam is a first laser beam, and the apparatus further comprises:

a second laser having a second laser beam which converges with the first laser beam in proximity to the operative site on the patient.

8. The electrosurgical apparatus recited in claim 7, wherein:

the first laser beam has properties including power, temperature, frequency, and cross sectional configuration; and the second laser beam has properties including power, temperature, frequency, and cross sectional configuration, respectively; and at least one of the properties of the first laser beam differs from the respective property of the second laser beam.

9. The electrosurgical apparatus recited in claim 1, wherein:

the electrosurgical apparatus includes a handpiece with a housing; and at least portions of the first delivery apparatus, second delivery apparatus, and third delivery apparatus are disposed within the housing of the hand piece.

10. The electrosurgical apparatus recited in claim 1, wherein the second delivery apparatus moves the laser beam to provide the pathway with a planar configuration.

11. An electrosurgical apparatus adapted to perform electrosurgery at an operative site on a patient, comprising:

a source of environmental gas providing gas molecules having properties for being energized at a particular frequency to an excited state;

first delivery apparatus coupled to the source of gas and adapted to deliver the gas molecules into proximity with the operative site;

a laser adapted to produce a laser beam providing laser energy at a frequency equal to about an integer multiple of the particular frequency of the environmental gas, and at a power generally sufficient to excite the gas molecules;

second delivery apparatus coupled to the laser for delivering the laser beam along a pathway leading toward the operative site;

an electrosurgery generator providing eleotrosurgical power;

third delivery apparatus coupled to the electrosurgery generator and adapted to deliver the electrosurgical power along the pathway toward the operative site;

a first jaw and an opposing second jaw;

the first delivery apparatus being disposed in the first jaw;

the second delivery apparatus being disposed in one of the first jaw and the second jaw; and the third delivery apparatus being disposed in one of the first jaw and the second jaw.

12. The eleotrosurgical apparatus recited in claim 11, wherein the second delivery apparatus is disposed in the first jaw and the third delivery apparatus is disposed in the opposing second jaw.

13. The electrosurgical apparatus recited in claim 11 wherein the second delivery apparatus includes a plurality of optical fibers.

14. The electrosurgical apparatus recited in claim 11, wherein the electrosurgery generator includes a first pole coupled to the first jaw and a second pole coupled to the second jaw.

15. An electrosurgical apparatus for performing laparoscopic electrosurgery at an operative site in the abdominal cavity of a patient, comprising:

a handpiece;

a source of environmental shielding gas providing gas molecules having properties for being energized at a particular frequency to an excited state;

first delivery apparatus carried by the handpiece and coupled to the source of gas, the first delivery apparatus being adapted to deliver the gas molecules into proximity with the operative site;

a laser carried by the handpiece and adapted to produce a laser beam providing laser energy at a frequency equal to about an integer multiple of the particular frequency of the environmental gas, and at a power generally sufficient to excite but not ionize the gas molecules;

second delivery apparatus coupled to the laser for establishing a pathway of excited gas molecules leading toward the operative site;

an electrosurgery generator providing electrosurgical power;

third delivery apparatus coupled to the electrosurgery generator and adapted to ionized the excited gas molecules along the pathway, and to deliver the electrosurgical power along the ionized pathway to the operative site;

a handpiece including a housing and an elongate probe extending from the housing; and at least the third delivery apparatus extending through the probe of the handpiece.

16. The eleotrosurgery apparatus recited in claim 15, wherein:

the second delivery apparatus extends through the probe of the handpiece.

17. The electrosurgery apparatus recited in claim 16, wherein:
the first delivery apparatus extends through the probe of the handpiece.

18. The electrosurgery apparatus recited in claim 15, wherein the source of gas is disposed in the housing of the hand piece.

19. The electrosurgery apparatus recited in claim 15, wherein the laser is disposed in the housing of the handpiece.

20. The electrosurgery apparatus recited in claim 19, wherein the source of gas is included in the housing of the handpiece.

21. The electrosurgery apparatus recited in claim 15, wherein the laser includes a battery and a laser generator powered by the battery.

22. The electrosurgery apparatus recited in claim 21, wherein the battery is rechargeable.

23. A catheter having a proximal end and a distal end, the catheter being adapted to perform electrosurgery within a body conduit, comprising:
an elongate shaft extending to the distal end of the catheter;
a balloon carried by the shaft and being disposed generally at the distal end of the catheter, the balloon having a wall and being inflatable by an inflation gas having molecules excitable by a laser;
portions of the balloon defining at least one hole providing for a controlled release of the inflation gas from the balloon;
inflation apparatus for inflating the balloon with the inflation gas and for releasing a portion of the inflation gas through the at least one hole in the balloon;
laser apparatus including a light fiber disposed along the wall of the balloon, the fiber being adapted to release laser energy into the inflation gas to excite the molecules of the gas along a pathway; and
electrosurgical apparatus including an electrode disposed along the wall of the balloon, the electrode being adapted to release electrosurgical energy along the pathway and to perform the electrosurgery within the body conduit.

24. The catheter recited in claim 23, wherein the wall of the balloon has an inner surface, and the light fiber is disposed along the inner surface of the balloon wall.

25. The catheter recited in claim 24, wherein the light fiber is a side-light fiber.

26. The catheter recited in claim 23, wherein the wall of the balloon has an outer surface and the electrosurgical electrode is disposed along the outer surface of the balloon wall.

27. The catheter recited in claim 26, wherein the light fiber of the laser apparatus is disposed along the outer surface of the balloon wall.

28. The catheter recited in claim 23, wherein:
the hole portions of the balloon, the light fiber of the laser system, and the electrode of the electrosurgery system are disposed generally longitudinally of the shaft of the catheter.

29. The catheter recited in claim 23, wherein the inflation gas has a excitation frequency and the laser energy of the laser apparatus has a discharge frequency equal to about an integer multiple of the excitation frequency.

30. An electrosurgical apparatus adapted to perform electrosurgery at an operative site on a patient, comprising;
a hand piece;
a source of environmental gas coupled to the handpiece and having gas molecules with properties for being energized at an excitation frequency;
a laser disposed in the handpiece to introduce a laser beam into the environmental gas to excite but not ionize the environmental gas along a pathway leading to the operative site on the patient;
the laser beam having a discharge frequency equal to about an integer multiple of the excitation frequency of the environmental gas; and
an electrosurgical generator coupled to the handpiece and disposed to create an electrosurgical arc along the pathway to perform the electrosurgery at the operative site on the patient.

31. The electrosurgical apparatus recited in claim 30, wherein the laser has an active medium with the discharge frequency.

32. The electrosurgical apparatus recited in claim 31, wherein the laser is a gas laser and the active medium is a gas.

33. The electrosurgical apparatus recited in claim 32, wherein the gas is carbon dioxide.

34. The electrosurgical apparatus recited in claim 31, wherein the laser is a solid state laser and the active medium is a crystal.

35. The electrosurgical apparatus recited in claim 34, wherein the crystal is ruby.

36. The eleotrosurgical apparatus recited in claim 31, wherein the discharge frequency of the laser is tunable.

37. A catheter adapted for operation with a laser end an electrosurgical generator, and in proximity to an environmental gas, comprising:
a catheter body extending along an axis between a proximal end and a distal end;
a hub disposed at the proximal end of the catheter body;
a delivery device disposed at the distal end of the catheter body;
an optical fiber included in the delivery device and adapted for connection to the laser to excite the environmental gas along a pathway leading to an operative site; and
an electrosurgical lead included in the delivery device and adapted for connection to the electrosurgical generator for delivering electrosurgical power along the pathway.

38. The catheter recited in claim 37, wherein the delivery device includes a balloon.

39. The catheter recited in claim 38, wherein the balloon is inflatable with the environmental gas.

40. The catheter recited in claim 38, wherein:
the optical fiber is disposed relative to the balloon; and
the electrosurgical lead is disposed externally of the balloon.

41. The catheter recited in claim 40, wherein the optical fiber is disposed interiorly of the balloon.

42. The Catheter recited in claim 37, wherein the electrosurgical lead is terminated distally at an electrode.

43. The catheter recited in claim 37, wherein the optical fiber is terminated at a refractive index coating.

44. The catheter recited in claim 43, wherein portions of the coating define a window permitting the escape of laser energy along the pathway.

45. An electrosurgical handpiece adapted for use with a source of environmental gas and an electrosurgical generator to perform an electrosurgical operation at an operative site, the handpiece comprising:
a housing;
a laser disposed in the housing;
at least one optical fiber coupled to the laser in the housing;
at least one electrosurgical electrode carried by the housing and adapted to be coupled to the electrosurgical generator;
a sheath enclosing the optical fiber and the electrode and defining a gas channel interiorly of the sheath and exteriorly of the optical fiber and the electrode;

the sheath being adapted for coupling the gas channel to the source of the environmental gas to direct the environmental gas toward the operative site;

the optical fiber being adapted for coupling to the laser to create a pathway of energized molecules of the environmental gas between the handpiece and the operative site; and the electrode being adapted for coupling to the electrosurgical generator for delivering electrosurgical power along the pathway.

46. The handpiece recited in claim 45 wherein the optical fiber is a first optical fiber and the pathway is a first pathway, the handpiece further comprises:

a second optical fiber disposed in the sheath and being coupled to the laser to create a pathway from energized molecules of the environmental gas between the handpiece and the operative site.

47. The handpiece recited in claim 46, further comprising:

a first lens for converging the pathway of the energized molecules from the first fiber toward the optical site and;

a second lens for converging the pathway of energized molecules from the second fiber toward the optical site.

48. The hand piece recited in claim 45, wherein the electrode is adapted for use in a bipolar electrosurgical configuration.

* * * * *

UNITED STATES PATENT AND TRADEMARK OFFICE
CERTIFICATE OF CORRECTION

PATENT NO. : 6,740,081 B2
APPLICATION NO. : 10/057227
DATED : May 25, 2004
INVENTOR(S) : Said Hilal It is certified that error appears in the above-identified patent and that said Letters Patent is hereby corrected as shown below:

In claim 9, column 11, line 56, please change "hand piece" to "handpiece"

Signed and Sealed this
Third Day of April, 2012

David J. Kappos
*Director of the United States Patent and Trademark Office*